(12) United States Patent
Bello et al.

(10) Patent No.: US 8,508,588 B2
(45) Date of Patent: Aug. 13, 2013

(54) METHODS AND SYSTEMS FOR IDENTIFYING WELL WALL BOUNDARIES OF MICROPLATES

(75) Inventors: Musodiq Olatayo Bello, Niskayuna, NY (US); Jens Rittscher, Ballston Lake, NY (US); Bikash Chandra Mahato, Bangalore (IN); Ahmad Yekta, Somerset, NJ (US); Jilin Tu, Schenectady, NY (US); Ying Li, New Brunswick, NJ (US)

(73) Assignee: General Electric Company, Niskayuna, NY (US)

( * ) Notice: Subject to any disclaimer, the term of this patent is extended or adjusted under 35 U.S.C. 154(b) by 722 days.

(21) Appl. No.: 12/783,297

(22) Filed: May 19, 2010

(65) Prior Publication Data

US 2011/0285837 A1    Nov. 24, 2011

(51) Int. Cl.
*H04N 9/47*     (2006.01)
*G06K 9/00*     (2006.01)
*G06K 9/46*     (2006.01)
*G02B 17/00*    (2006.01)
*G01N 23/00*    (2006.01)
*A61B 3/14*     (2006.01)

(52) U.S. Cl.
USPC ............. 348/79; 382/190; 382/133; 382/128; 359/726; 250/311; 351/206

(58) Field of Classification Search
USPC .................................... 348/79; 382/190, 133
See application file for complete search history.

(56) References Cited

U.S. PATENT DOCUMENTS

| | | |
|---|---|---|
| 4,115,010 A | 9/1978 | McAleer et al. |
| 2004/0233545 A1* | 11/2004 | Jiang et al. .................... 359/726 |
| 2006/0291706 A1* | 12/2006 | Gunstream et al. ........... 382/128 |
| 2007/0158568 A1* | 7/2007 | Nakamura et al. ............ 250/311 |
| 2009/0268159 A1* | 10/2009 | Xu et al. ....................... 351/206 |

OTHER PUBLICATIONS

Lee, "Robust Image Segmentation Using Active Contours: Level Set Approaches", A dissertation submitted to the Graduate Faculty of North Carolina State University in partial satisfaction of the requirements for the Degree of Doctor of Philosophy, Department of Electrical and Computer Engineering, Raleigh, North Carolina, 146 pages, 2005.

* cited by examiner

*Primary Examiner* — Sath V Perungavoor
*Assistant Examiner* — Xiaolan Xu
(74) *Attorney, Agent, or Firm* — Eileen B. Gallagher

(57) ABSTRACT

The present invention is directed to method and system for image processing of test wells on a microplates wherein the microplates' test well wall boundaries are identified through the use of a candidate edge image wherein the candidate edge image represents locations of one or more segments of the wall boundaries.

17 Claims, 3 Drawing Sheets

A  B

A  B

METHODS AND SYSTEMS FOR IDENTIFYING WELL WALL BOUNDARIES OF MICROPLATES

BACKGROUND

Figure 1:
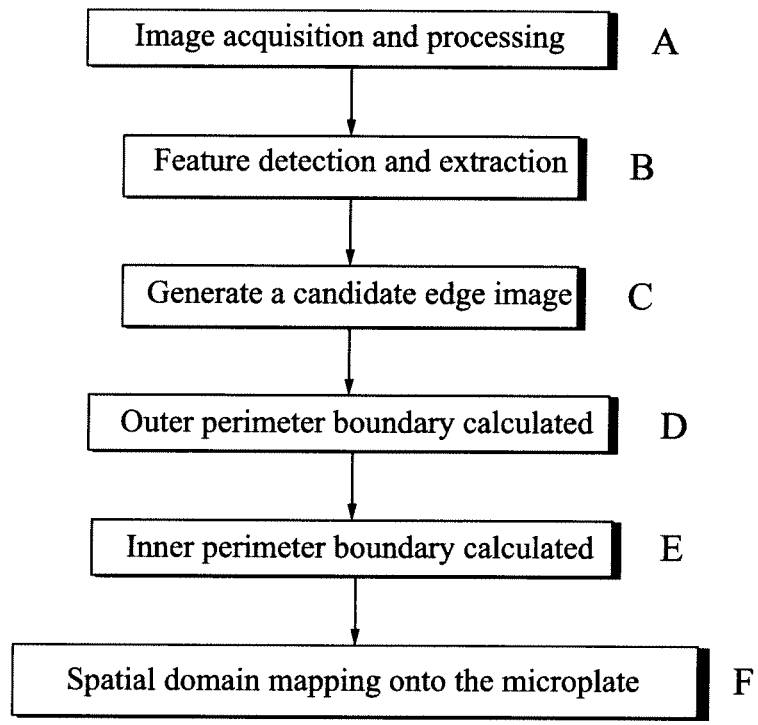

Microtiter plates or microplates have become a standard tool in analytical research and clinical diagnostic testing laboratories. They are commonly used in a variety of detection procedures, which involve an image acquisition system such as fluorescence, luminescence, radiometric, absorbance, and light imaging. A microplate typically has 6, 24, 96, 384 or more sample wells arranged in a rectangular matrix and each well is designed to hold samples such as cell and tissue cultures as well as whole organisms such as the zebrafish.

In high-throughput microscopy, an image acquisition system, attached to a microscope, can be configured to image an entire well plate mounted onto the stage of the microscope, as a single image in one or more field of views, or each test well separately, also with one or more field of views. While most microplates consists of circular wells, rectangular wells are not uncommon. Each well of a microplate may hold between tens of nanoliters to several milliliters of liquid.

In some systems, a scan plan may be used to direct the imaging across the surface of the microplate. In the simplest method, the system must look at the entire microplate and identify the location of the test samples, which typically are cell and tissue cultures, or organisms. The test sample is then converted to a region envelope. The coordinates of the region are then mapped in the position space of the microscope stage. This allows the microscope motion to be programmed to cover the appropriate areas of the microplate, and avoid areas of waste between the tissue samples, or in the case of a microplate, sample wells that do not contain a sample. The scan plan may also be referred to as an illumination mask wherein, certain regions of the microplate that are masked out are not imaged. However, manually generating a scan plan can be time consuming and often may not be accurate.

Therefore an alternative process to provide high throughput image processing of microplates is desirable, such as a process to efficiently detects the microplate's sample well wall boundaries. Accurately identifying the location of the well wall can be used to speed up high-resolution image acquisition of relevant parts of the plate and may also be used in a pre-processing step for subsequent image acquisition and image analysis of the microplate. As such, a mask of the inner well regions can help to avoid unnecessary processing outside the well wall and improve the speed of downstream image processing. A mask can also help to reduce the complexity of illumination correction or flat field correction where there are bright spots within or outside the well.

BRIEF DESCRIPTION

The present invention is directed to method and system for image processing of test wells on a microplate wherein the microplate's test well wall boundaries are identified.

In one embodiment of the invention a method of locating the wall boundaries of test wells arranged on the surface of a microplate is described. The method comprises illuminating a microplate and capturing a digital image, analyzing the image utilizing, at least in part, pixel intensity information to detect features of the wall boundaries of the test wells, and generating a candidate edge image using the features of the wall boundaries which represents locations of one or more segments of the wall boundaries. The method further comprises analyzing the candidate edge image to calculate the spatial location of the outer perimeter boundary of one or more test wells and using that information to determine the spatial location of the inner perimeter boundary. The spatial domains of the boundaries are then mapped on the surface of the microplate to identify test well regions.

In a second embodiment of the invention an apparatus for locating wall boundaries of test wells arranged on the surface of a microplate is disclosed comprising an imaging microscope, an excitation source, a digital image device, a storage device, and a processor. The processor is capable of analyzing a digital image of the microplate utilizing, at least in part, pixel intensity information to detect features of the wall boundaries of the test wells and generating a candidate edge image of the microplate which represents locations of one or more segments of the test wall boundaries. The processor is further capable of analyzing the candidate edge image using an algorithm to calculate the outer perimeter boundary of one or more test wells. The spatial location of the outer perimeter boundary is then used to determine the spatial location of the inner perimeter boundary. Using this information, a binary image of the microplate is generated which is a spatial domain image of the location of the test wells. This information may be mapped on to the surface of the microplate to identify test well regions.

DRAWINGS

These and other features, aspects, and advantages of the present invention will become better understood when the following detailed description is read with reference to the accompanying drawings in which like characters represent like parts throughout the drawings.

Figure 2:
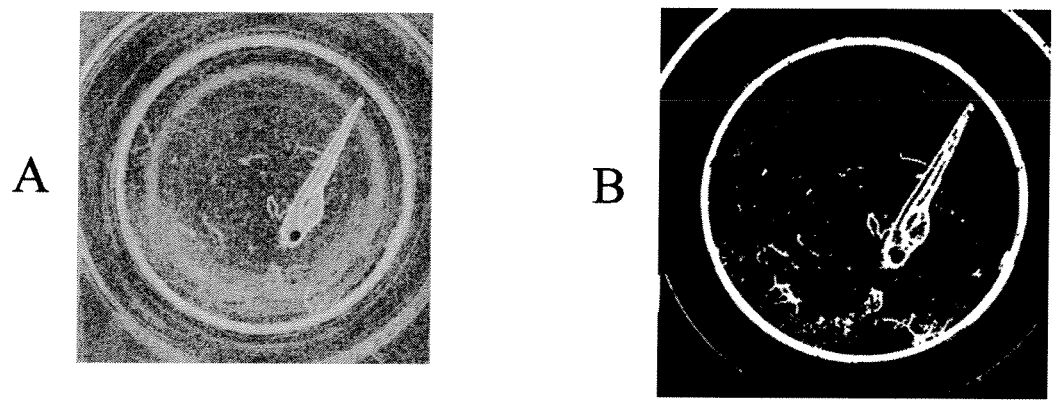

FIG. 1 is a flow diagram showing a method of identifying test well wall boundaries on a microplate FIG. 2 are micrographs showing the extraction of features from a typical image and the generation of candidate edges; A illustrates points in the image with features of interest and B shows the down-selection of the points to obtain candidate edges.

Figure 3:
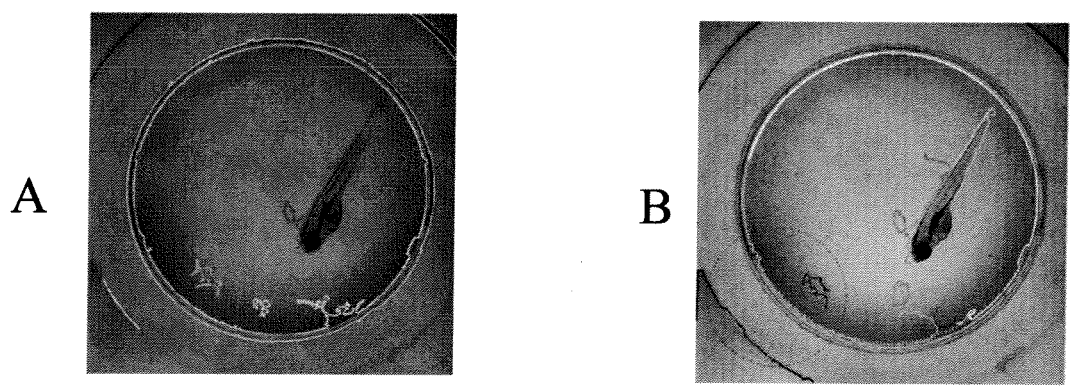
Figure 3:
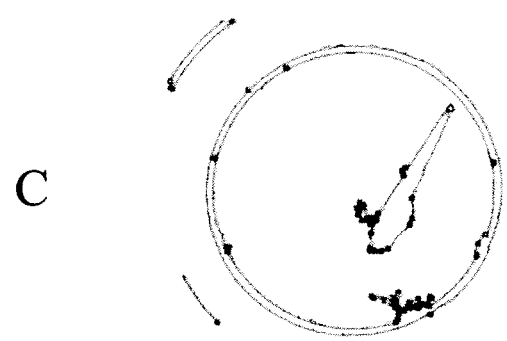

FIG. 3 are micrographs illustrating contour extraction; A illustrates contours extracted from the candidate edges overlaid on the original image used for FIG. 2; B illustrates the corresponding circles fitted to the contours; C illustrates the process of analyzing curvature points on the contour to obtain optimal arcs.

Figure 4:
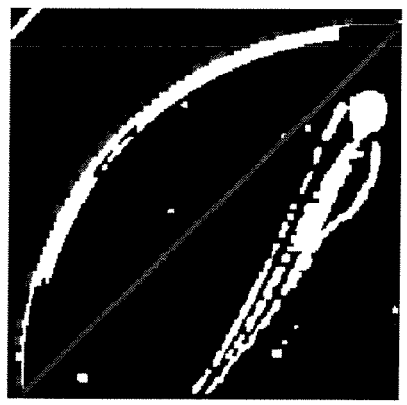
Figure 4:
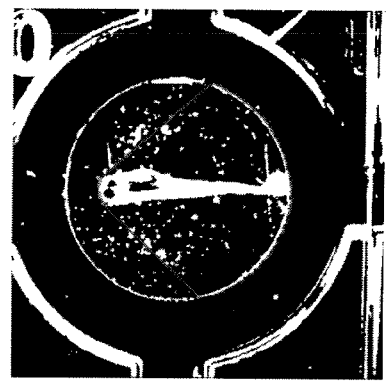

FIG. 4 is micrographs showing the results of a convex hull analysis of test well walls.

Figure 5:
Figure 5:
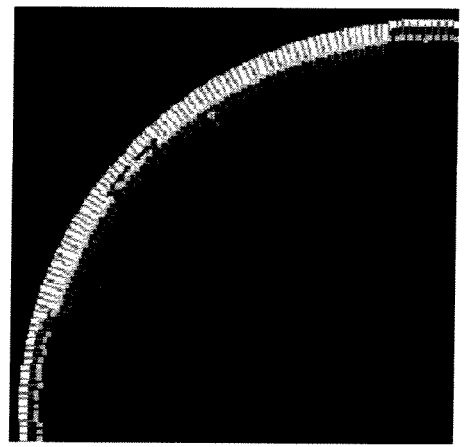

FIG. 5 is micrographs showing estimation of the inner boundary. A shows the direction of tracing from the outer boundary; B shows the estimation of the well wall thickness.

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Samples" refer to the chemical or biological test materials, which are contained within the test wells of the microplate. The samples may be cell and tissue cultures as well as whole organisms such as the zebrafish. A test well may also contain one or more samples such as multiple organisms. Common detection modes include, but are not limited to, absorbance, fluorescence intensity, luminescence, time-resolved fluorescence, and fluorescence polarization.

The tissue sample may also be part of a tissue microarray (TMA). As such the tissue sample is one of multiple samples contained within test wells arranged on a single slide. The number of test wells, and therefore the number of individual tissue samples on the single slide, is variable depending on the array design. For example, a TMA may be designed such that each individual tissue sample comprises circular test wells that are 0.6 mm in diameter at a spacing of 0.7-0.8 mm resulting in a surface area of each tissue sample of 0.282 mm$^2$. Larger and smaller TMA are also readily available.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

The invention includes embodiments that relate generally to methods applicable in analytical, diagnostic, or prognostic applications such as high-content screening, high-content analysis, analyte detection, histochemistry, immunohistochemistry, or immunofluorescence.

The disclosed invention describes a method wherein the boundaries of test wells arranged on the surface of a microplate are identified in a low-resolution scan and a binary, spatial image of the test wells is created. The binary, spatial image may then be used in the analysis of the samples in the test wells. For example, an illumination mask locating the inner well regions can be used to avoid unnecessary processing outside the well wall and improve the speed of downstream analysis. Also, well wall detection can be used to create a scan plan to direct the microscope during image acquisition. By correctly identifying the boundaries of the well plates in a low resolution scan, the microscope can be directed to image only inside the well walls in a higher magnification scan to increase scan throughput and reduce image storage requirements. Well wall detection may also be a preprocessing step for illumination correction algorithms where the inner and outer regions of the well are treated differently. The method involves detecting the well wall in one or both brightfield and fluorescent images, even if only a part of the wall is contained in the image or if the wall is partially occluded, and whether the well contains samples or not.

FIG. 1 is a flow diagram showing a method that may be used to detect the boundaries of the test wells. In one embodiment, as shown in FIG. 1, an image acquisition and processing step (A) is used to obtain images from the well plate, which may be obtained in brightfield or fluorescent microscopy. Features of the test wells, arranged on the well plate, are detected and extracted from the image (B) based, at least in part, on pixel intensity information. In certain embodiments, the features of the image to be detected and extracted may include, but not limited to, intensity features, edge features, eigen values for the evaluation of curvature, texture features, tubularity features, corner detection features, line thickness features, line continuity features, gray level features, or combinations thereof.

As shown further in FIG. 1, the extracted features are analyzed and reconstituted to form a candidate edge image, which represents locations of one or more segments of the possible wall boundaries (C). Generating the candidate edge image may comprise a number of methods including, but not limited to, applying edge detection filters, pixel threshold values, contour extraction modules, Hough transform, pixel classification and clustering, or combinations thereof.

The candidate edge image is further analyzed, to calculate the outer perimeter boundary of one or more of the test wells (D). In certain embodiment, using the location of the outer perimeter boundary and pixel information from the low-resolution image, the inner perimeter boundary of one or more of the test wells is also calculated (E). The result is a binary image of the location of the boundaries of the test wells. The boundaries may be the inner boundary, the outer boundary or both. The well boundary image may then be used to create an image map of the spatial location of the well boundaries of the microplate useful in scan planning, creating an illumination mask, or downstream analysis (F).

Often the images captured from the microplates are large and require long processing times. For example, images of a well in a microplate may be captured in a single view with a camera at a resolution of 2048×2048 pixels. In certain embodiments the image processing step (A) may involve down sampling the image to increase processing speed without diminishing the accuracy of feature detection. As such down sampling of 25% of the aforementioned well plate would result in a 512×512 pixels resolution. In certain embodiments, down sampling may also be accompanied by Gaussian smoothing.

Once the image is obtained, in order to detect and extract selected features, filters may be applied to the image. In certain embodiments, simple horizontal and vertical Sobel filters may be used to assign a gradient magnitude value to each pixel based on pixel intensity. A threshold value is dynamically chosen based on the statistics of the edge image and those pixels below the threshold value are suppressed, creating a candidate edge image.

For example, letting $E_h$ and $E_v$ be the horizontal and vertical Sobel edge images respectively, for each corresponding pixel an edge magnitude image $E_r$, is computed as $$E_m = \sqrt{E_h^2 + E_v^2}.$$

The result is the gradient of image intensity at each pixel site. A histogram of the computed Em value is created and analyzed where only pixels with gradient in the top p % range, where p is typically a numerical value between top 5%-10%, are selected. These selected pixels may be used to create a binary edge image, since edges usually have high intensity gradient.

In other embodiments, two threshold values may be applied. For example, pixels are selected using a 5% threshold based on those pixels showing the highest intensity values. A second series of pixels is then selected based on a 10% threshold. A hysteresis thresholding method is used in analyzing both sets of pixels to obtain a candidate edge image. The method works by considering pixels values above the second threshold level and having a nearest neighbor with pixel value above the first threshold level. The candidate edge image might have areas that are incomplete, voids that are corrected using the two-step processing on the candidate edge image. Further correction, or morphological closing, of the candidate image may be performed to generate a smooth and realistic edge map.

In certain embodiments, contour extraction may be applied to the candidate edge image using a contour extraction module, such as cvFindContour available in the OpenCV (Open Source Computer Vision) library, wherein the contours in the binary edge image are identified. From the set of contours extracted out from the binary edge image, candidate contours of well wall are selected using a rule-based method. A rule-based method may include setting a specified minimum length, and eliminating contours, that are detected but are less than the minimum length. For example, referring to a circular well, a minimum expected circumference may be computed based on the known dimensions of the wells in a given well plate, or based on the dimension of the acquired image. When detecting the wall of a circular well plate, the contours may also be fitted to a circle and contours with high residual errors eliminated.

In certain instances, contour detection may be affected by the presence of artifacts in the image or the organism being imaged touching the well wall. An attempt to fit the contour, as detected, may produce large residual errors. In order to avoid this, in certain embodiments a best arc analysis may be used wherein the longest segment of the contour resembling a circle is selected by computing contour-to-circle similarity metrics. Since the contour along a circle is expected to be uniform, discontinuous points of high curvature are indications of artifacts or undesired object-well wall interactions. These points may be discarded. As such, the contours are separated or broken at these points of high curvature, to obtain arcs, which can then be independently processed.

In certain embodiments, adjacent arcs are merged in order to obtain the longest 'best arc' possible. FIG. 3 is a series of micrographs, which illustrates the analysis of curvature on contours of a typical candidate edge image using the test well images shown in FIG. 2. FIG. 3 image A shows the extracted contours overlaid on the original image; B illustrates the fitted circles corresponding to the contours; C shows the process of breaking up the contours into arcs and segments and subsequent merging of adjacent arcs.

In one embodiment, a circle fitting analysis may be used to estimate the circle corresponding to a given contour or arc of a contour. For example the equation for points 0, 1, 2, ..., n on the contours of a circle where the center $(x_c, y_c)$ and radius, r, are unknowns may be written as:

$$\left. \begin{aligned} (x_0 - x_c)^2 + (y_0 - y_c)^2 &= r^2 \\ (x_1 - x_c)^2 + (y_1 - y_c)^2 &= r^2 \\ &\cdots \\ (x_n - x_c)^2 + (y_n - y_c)^2 &= r^2 \end{aligned} \right\}.$$

This can be written as a set of linear equations of the form:

$$AX = B,$$

where $$A = \begin{bmatrix} x_0 & y_0 & 1 \\ x_1 & y_1 & 1 \\ \vdots & \vdots & \vdots \\ \vdots & \vdots & \vdots \\ x_n & y_n & 1 \end{bmatrix},$$

and $$B = \begin{bmatrix} D_0 \\ D_1 \\ \vdots \\ \vdots \\ D_n \end{bmatrix} \text{ where } \ldots D_i = -(x_i^2 + y_i^2).$$

The solution of this system of equations is $$X = \begin{bmatrix} X \\ Y \\ C \end{bmatrix}.$$

From the solution in Eq. 6, the center of the circle can be computed as $$\left. \begin{aligned} x_c &= -0.5X \\ y_c &= -0.5Y \end{aligned} \right\}$$

and the radius is computed as $$r = \frac{\sqrt{X^2 + Y^2}}{4} - C.$$

Based on the center and radius, a polygon P representing a circle may be generated by sampling θ at, 1-degree intervals. Each point on P is computed as:

$$\left. \begin{aligned} x_i' &= x_c + r \cdot \cos(i \cdot \pi / 180) \\ y_i' &= y_c + r \cdot \sin(i \cdot \pi / 180) \end{aligned} \right\}. \quad i = [0, 360].$$

The above formulation is used to estimate the circle corresponding to each contour/arc. Both contour-to-circle metric, mean/median distance between points on the contour and the corresponding closest point on the fitted circle, and circle-to-contour metric in which the distance from every point on the circle polygon is computed to the nearest point on the contour, may be used to assess the fit of the contour to the circle. The algorithm iteratively processes all the contours in the image and considers only the best-fit circles. The best fitting of a circle is considered if the mean/median distance between points on the contour and the fitted circle as well as the contour-to-circle metric, is below a threshold value. Among the best-fit circles, a single circle is selected through analyzing the mean/median distance and the corresponding well radius.

In certain embodiments, a region analysis method may be used for well wall selection and extraction from the well wall candidate edge image. This involves generating convex hulls around candidate well wall, which may be whole or partial regions. Convex hull is defined as the boundary of the minimal convex set containing a given non-empty finite set of points in a given plane. Unless the points are collinear, the convex hull is a simple closed polygonal chain. The equation representing the convex hull is usually estimated in terms of n, the number of input points, and h the number of points on the convex hull. Since a circle is a convex structure, the calculated convex hull of a circle will still be a circle. The convex hull overlaps perfectly with the circular boundary present in the region and does not overlap properly with non-boundary segments.

This is illustrated in FIG. 4 which is micrographs showing the results of a convex hull analysis of a detected partial test well wall. Selecting the longest smooth piece of the convexes that overlaps with edges in the edge map, gives the circular part of the region boundary. In order to improve the robustness of the candidate selection method, particularly in cases where the sample in the well may be attached to the well wall, preference is given to convex hull regions with (a) larger area or area comparable to the known area of the wells, b) similar height and width since this is expected in a circular well, and c) dimensions above the threshold of being simply noise or artifacts.

Referring again to FIG. 1, the candidate images are further analyzed, to further refine the candidate image and calculate a binary image of the inner perimeter boundary (E) from the outer perimeter boundary (D). A well wall refinement step may also be used to intensify the inner boundaries of the test well. The information is used to generate a well boundary image. The well boundary image may then be used to create an image map of the spatial location of the well boundaries of the microplate useful in scan planning, creating an illumination mask, or downstream analysis (F).

Steps (D) and (E) may be used in images wherein the entire well wall, or only a segment of the well wall is visible.

In cases where only a partial well wall is present in the image, the detected circular well wall may not be accurately centered on the image due to the small size of the arc used to estimate the circle. The circle detection may be further improved using the Hough transform. The approximate radius of the well is calculated by using a fitted circle. A ring shape region of interested is selected based on the approximate radius to dramatically reduce the running time of the Hough transform algorithm.

Once the circular outer boundary is identified, the circular outer boundary may be traced along the perpendicular direction to identify the inner boundary of the well wall, step (E). In certain embodiments, this may be accomplished by assuming that the thickness of the well wall is constant for the entire perimeter of a given well. To locate the inner well wall, an equal distance point is traced around the outer boundary. For example, each point on the outer boundary is traced along the perpendicular direction in a stepwise fashion and the pixel intensity is recorded. Consecutive pixels having the same intensity are identified as being part of the well wall. If the tracing, pixels having the same intensity, is longer than a pre-defined distance, such as 15% of the radius of the well, the thickness at this point will not be recorded as the measurement suggest that part of the sample or an anomaly is attached to the wall at that point. After all the points on the outer boundary are traced, the thickness of the well wall is estimated using a majority voting method. The estimated thickness is applied to the image and points along the inner wall. The positions of the inner wall points achieved by the tracing are adjusted according to the estimated well wall thickness.

An example of the estimation technique is shown in FIG. 5, which illustrates tracing result of the well wall. FIG. 5A illustrates the tracing direction of each point on the outer boundary. FIG. 5B shows individual points on the outer boundary traced towards the inner boundary, and the final position of the points on the inner well wall after adjustment using the estimated well wall thickness based on majority vote.

The method described was successfully tested using 340 images of 6.4 mm circular wells, 100 images of 4.5 mm circular wells, and 96 slide images having no well present. For the 6.4 mm well images, 100% of the result image plan aligned with that of the actual inner well wall. For the 4.5 mm well images, 11% of the wells were not identified resulting from low contrast between the well wall and the background, as well as a 1% false positive detection. For the 96 slide images, having no well walls, 0% false positive well walls were detected, a 100% success rate. To improve the detection accuracy even further, user provided information about size and shape of the well may be applied.

In certain embodiments, additional digital images of the microplate may be acquired using the spatial domain map or illumination mask. This may allow higher resolution images to be acquired while avoiding regions outside the well walls. It may also provide a method of correcting the lateral positioning of the XY stage to center the well in the image plane.

In still other embodiments, data from prior images or from the microarray dimensions may be used to augment the generation of the well boundary image. For example information related to the general shape of the test wells, size range or placement on the microscope stage may be used to eliminate or reduce the number of potential candidate images. This may result in improving the process in a number of areas such as, but not limited to acquisition speed, resolution settings, signal to noise ratio, fidelity, specificity, or a combination thereof.

Similar to microplates having circular wells, microplates having rectangular wells may also be analyzed and the inner and outer boundaries identified. Unlike circular wells, the boundaries are more rectangular and therefore may be detected as a collection of straight lines.

In one embodiment, Hough transform may be used to detect straight lines in the image. Orthogonal straight lines are connected to form boxes, or potential well wall boundaries. The area inside and outside the box may be analyzed. The box that maximizes the difference between the inside and outside regions may be select as the well boundary. A similar tracing procedure, used for circular well walls, may then used to estimate the thickness of the well wall.

In another embodiment, a straight line is placed on one edge of the image and the line is progressively moved inwards towards the center of the image. Texture features on both sides are analyzed and the point of maximal difference between opposite sides of the line is noted. At this point, the line is rotated within +30 to −30 degrees to account for the possibility of the well wall being slightly rotated. A similar procedure is repeated for the three other sides of the image. Lines from one or two sides of the image may be dropped if the texture difference on opposite sides is not significant. This is an indication that the image only includes part of the well and the inside of the well wall is touching the sides of the image. The accepted lines are then taken as sides of the well.

Since background intensity usually varies between the inside and the outside of the well, in yet another embodiment, all pixels in the image may be clustered using intensity features in a local neighborhood after an initial smoothing of the image. By setting the number of clusters between 3 and 5, the outside of the well may be selected as the cluster region closest to the edges of the image. The well boundary may then be obtained from the internal portion of this region.

In all the embodiments for rectangular wall detection, a similar tracing procedure used for circular well walls may be used to estimate the thickness of the well wall.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method of locating the wall boundaries of test wells arranged on the surface of a microplate comprising:
   illuminating a microplate and capturing a digital image of said microplate;
   analyzing the digital image of the microplate utilizing, at least in part, pixel intensity information to detect features of the wall boundaries of the test wells;
   generating a candidate edge image of the microplate using the features of the wall boundaries wherein the candidate edge image represents locations of one or more segments of the wall boundaries;
   analyzing the candidate edge image using an algorithm to calculate the outer perimeter boundary of one or more test wells and to determine the spatial location of the outer perimeter boundary on the surface of the microplate;

analyzing the outer perimeter boundary of the one or more test wells utilizing, at least in part, pixel intensity information to determine the spatial location of the inner perimeter boundary of one or more test wells;

mapping the spatial domain image of the boundary on the microplate to identify test well regions on the surface of the microplate.

2. The method of claim 1 wherein the features of the wall boundaries comprises, intensity features, edge features, eigen values for the evaluation of curvature, texture features, tubularity features, corner detection features, line thickness features, line continuity features, gray level features, or combinations thereof.

3. The method of claim 1 wherein generating a candidate edge image comprises applying edge detection filters, pixel threshold values, contour extraction modules, Hough transform, pixel classification and clustering, or combinations thereof.

4. The method of claim 1 wherein the calculating the outer perimeter boundary of one or more test wells comprises a circle fitting analysis, best arc analysis, rectangular fitting analysis, convex hull analysis, Hough transform, evaluating residual error in fitting the contours to models of circles or rectangles, analyzing texture features on opposite sides of potential boundaries or a combination thereof.

5. The method of claim 4 the calculating the outer perimeter boundary of one or more test wells comprises a convex hull analysis.

6. The method of claim 1 further comprising a well wall refinement step to detect the inner perimeter boundary of the well by tracing inwards from the outer boundary and selecting an inner boundary by majority vote.

7. The method of claim 1 wherein the mask of the detected well wall is mapped to the domain of the microplate.

8. The method of claim 1 further comprising generating a scan plan, an illumination mask, or a combination thereof for analyzing the microarray wherein the microarray contains test samples.

9. The method of claim 8 further comprising capturing additional digital image of said microplate based on the scan plan, illumination mask, or a combination thereof.

10. The method of claim 8 wherein the test samples comprise cell cultures, tissue cultures, whole organisms, or combinations thereof.

11. An apparatus for locating wall boundaries of test wells arranged on the surface of a microplate comprising:

an imaging microscope having at least one objective lens to acquire images at one or more magnifications and a stage to hold the microplate;

an excitation source to illuminate the microplate on the stage;

a digital image device connected to the microscope to acquire a digital image of the microplate;

a storage device in communication with the digital image device capable of storing the digitized images of the microplate; and a processor in communication with the storage device and capable of;

analyzing the digital image of the microplate utilizing, at least in part, pixel intensity information to detect features of the wall boundaries of the test wells;

generating a candidate edge image of the microplate using the features of the wall boundaries wherein the candidate edge image represents locations of one or more segments of the wall boundaries;

analyzing the candidate edge image using an algorithm to calculate the outer perimeter boundary of one or more test wells and to determine the spatial location of the outer perimeter boundary on the surface of the microplate;

analyzing the outer perimeter boundary of the one or more test wells utilizing, at least in part, pixel intensity information to determine the spatial location of the inner perimeter boundary of one or more test wells;

generating a binary image of the microplate wherein the binary image is a spatial domain image of the location of the inner and outer boundaries of the test wells; and mapping the spatial domain image on the microplate to identify test well regions on the surface of the microplate.

12. The apparatus of claim 11 wherein the digital image device is configured to acquire one or more additional digital images of the microplate using the binary image acquired from the first digital image.

13. The apparatus according to claim 11 further comprising a display device for displaying the digitized images of the microplate.

14. The apparatus according to claim 11 further comprising a controller and a machine-readable medium comprising instructions which when executed by the controller causes an apparatus to locate the inner and outer boundaries of the test wells.

15. The apparatus according to claim 11 wherein the apparatus is incorporated as components of an analytical device.

16. The apparatus of claim 14 wherein the analytical device is capable of staining and imaging microplates.

17. The apparatus of claim 11 wherein the microplate is a tissue-micro array.

* * * * *

UNITED STATES PATENT AND TRADEMARK OFFICE
CERTIFICATE OF CORRECTION

PATENT NO. : 8,508,588 B2
APPLICATION NO. : 12/783297
DATED : August 13, 2013
INVENTOR(S) : Bello et al.

It is certified that error appears in the above-identified patent and that said Letters Patent is hereby corrected as shown below:

On the Title Page, in Item (57), under "ABSTRACT", in Column 2, Line 2, delete "on a" and insert -- on --, therefor.

In the Specification

In Column 2, Line 35, delete "microplate" and insert -- microplate. --, therefor.

In Column 2, Line 47, delete "is micrographs" and insert -- are micrographs --, therefor.

In Column 2, Line 49, delete "is micrographs" and insert -- are micrographs --, therefor.

In Column 4, Line 32, delete "$E_r$," and insert -- $E_m$ --, therefor.

In Column 4, Line 34, delete "$E_m = \sqrt{\sqrt{E_h^2 + E_v^2}}.$" and insert -- $E_m = \sqrt{E_h^2 + E_v^2}.$ --, therefor.

In Column 6, Line 53, delete "is micrographs" and insert -- are micrographs --, therefor.

In the Claims

In Column 9, Line 29, in Claim 5, delete "the calculating" and insert -- wherein the calculating --, therefor.

Signed and Sealed this
Nineteenth Day of November, 2013

Teresa Stanek Rea
*Deputy Director of the United States Patent and Trademark Office*